(12) United States Patent
Lee

(10) Patent No.: US 6,605,576 B2
(45) Date of Patent: Aug. 12, 2003

(54) ARTIFICIAL NAIL REMOVER

(75) Inventor: Cheon Sook Lee, Seoul (KR)

(73) Assignees: Y. S. Creation Co. Ltd., Seoul (KR); Meepo U.S.A. Co., Arcadia, CA (US)

(*) Notice: Subject to any disclaimer, the term of this patent is extended or adjusted under 35 U.S.C. 154(b) by 97 days.

(21) Appl. No.: 09/957,466

(22) Filed: Sep. 20, 2001

(65) Prior Publication Data

US 2003/0054964 A1 Mar. 20, 2003

(51) Int. Cl.[7] .................................................. C11D 3/44
(52) U.S. Cl. ........................ 510/118; 510/134; 510/138; 134/38; 424/61; 424/401
(58) Field of Search ..................... 424/401, 61; 134/38; 510/118, 134, 138

(56) References Cited

U.S. PATENT DOCUMENTS 5,582,333 A * 12/1996 Bennett ..................... 222/546

* cited by examiner

Primary Examiner—Gregory E. Webb
(74) Attorney, Agent, or Firm—Raymond Sun

(57) ABSTRACT

An artificial nail remover includes the following ingredients: acetone, methyl ethyl ketone, ethanol, dimethyl esters, Glycerine, water, vitamin E, and a perfume.

8 Claims, 1 Drawing Sheet

ARTIFICIAL NAIL REMOVER

BACKGROUND OF THE INVENTION

1. Field of the Invention

The present invention relates to a nail remover that is used to remove artificial nails.

2. Description of the Prior Art

Artificial nails are currently very popular. Unfortunately, all artifical nails eventually need to be removed. Most conventional artificial nails are made primarily of Acrylonitride Butadiene Styrene (ABS), which is a type of plastic material. Cyanoacrylate (which is the primary ingredient of glue) is typically used to attach the artificial nail to the user's real nail. At this time, acetone is most commonly used to remove artificial nails, and functions to decompose cyanoacrylate. The removal process typically involves soaking the artificial nail in a container that contains acetone for a period of time. Unfortunately, the use of acetone as an artificial nail remover has created problems of chlorosis, the removal of fat, and the creation of a strong and unpleasant odor. Chlorosis is the condition where the acetone dries and the remaining material reacts with air and remains on the surface of the white, which becomes white.

Thus, there remains a need for an improved artificial nail remover that can effectively remove artificial nails while overcoming the drawbacks mentioned above.

SUMMARY OF THE DISCLOSURE

It is an object of the present invention to provide a remover that can effectively remove artificial nails.

It is another object of the present invention to provide an artificial nail remover that avoids the problems of chlorosis, the removal of fat, and the creation of a strong and unpleasant odor.

The objectives of the present invention are accomplished by providing an artificial nail remover that includes the following ingredients: acetone, methyl ethyl ketone, ethanol, dimethyl esters, Glycerine, water, vitamin E, and a perfume.

DETAILED DESCRIPTION OF THE PREFERRED EMBODIMENTS

Figure 1:
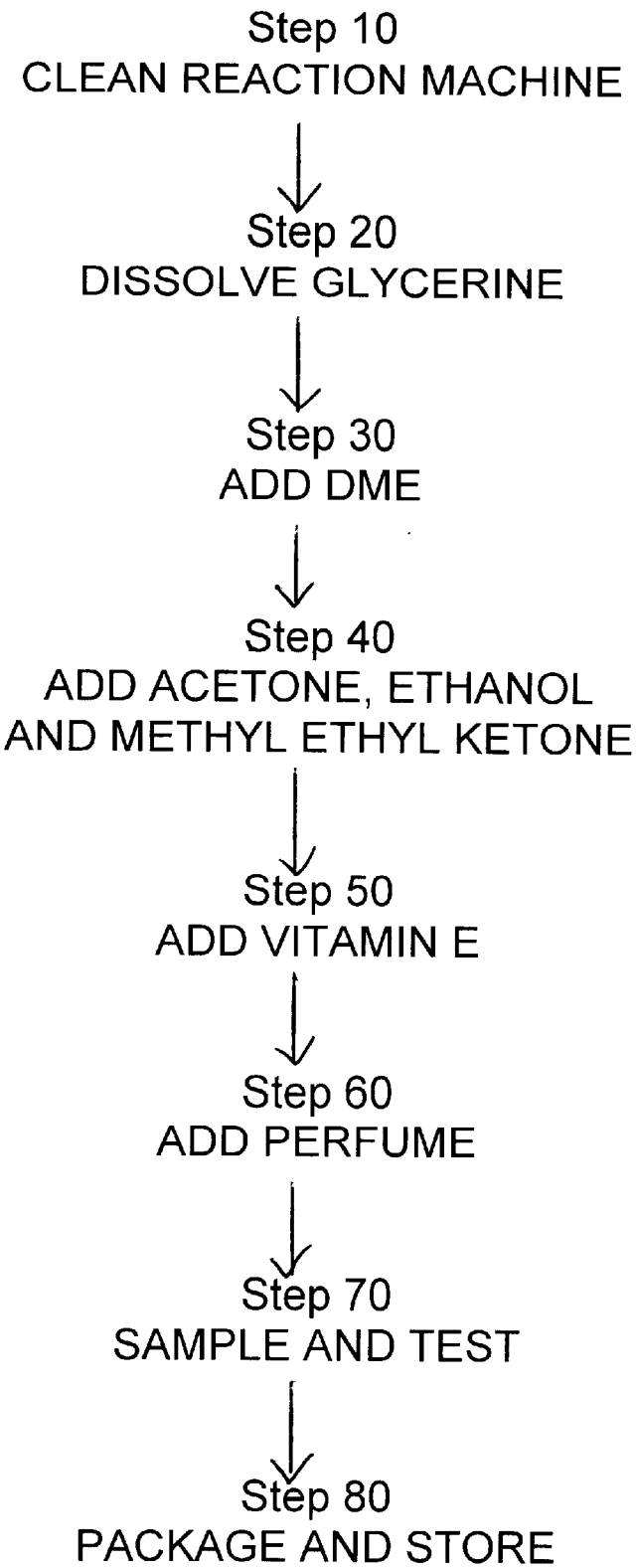
FIG. 1 is a flowchart illustrating a method of manufacturing an artificial nail remover according to one embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

The present invention provides an artificial nail remover that effectively removes an artificial nail very quickly, while avoiding the problems of chlorosis, the removal of fat, and the creation of a strong and unpleasant odor. The artificial nail remover according to one non-limiting embodiment of the present invention has the following ingredients:

| Ingredient | Approximate Percentage |
| --- | --- |
| Acetone | $\leq 40\%$ |
| Methyl Ethyl Ketone | $\leq 25\%$ |
| Ethanol | $\leq 5\%$ |
| Dimethyl esters | $\leq 15\%$ |
| Glycerine | $\leq 7\%$ |
| Water | $\leq 3\%$ |
| Vitamin E | $\leq 1\%$ |
| Perfume | $\leq 4\%$ |

As shown above, the primary component is acetone, but other components are added to address some of the problems experienced by the conventional nail removers.

For example, glycerin is added to minimize chlorosis and the removal of fat. Vitamin E is added to moisturize and otherwise supplement the user's skin. The perfume gives off a fragrance, and is added to counter or offset the normal strong and unpleasant odor of acetone. Here, the perfume can be flavored, and can include flavors such as cucumber, rose, lavendar, etc.

In addition, dimethyl esters (DME) are added to achieve restraint from acetone volatility, and in particular, to prevent the acetone from evaporating. This function is to maximize the dissolving effect with small amounts of acetone to provide prolonged dissolving effect.

Moreover, the Methyl Ethyl Ketone and the Ethanol function to assist the acetone in melting the ABS material of the artificial nail.

FIG. 1 illustrates one non-limiting method of manufacturing the artificial nail remover of the present invention. In step 10, the reaction machine that is used to make the nail remover is cleaned. This reaction machine includes a temperature sensor and an electrical heating device, and can have a capacity of 200 liters. The reaction machine can also have a cover or lid that can be opened and closed to introduce ingredients. In step 20, glycerin is mixed with water in a ratio of 7:3 for glycerin to water. The mixing is done for three minutes at 25 degrees Celcius in the reaction machine. In step 30, the DME is added to the glycerin and water mixture, and then mixed for five minutes at 25 degrees Celcius in the reaction machine. In step 40, the acetone, Ethanol, and Methy Ethyl Ketone are added to the existing DME, glycerin and water mixture, and then mixed for ten minutes at 25 degrees Celcius in the reaction machine. The cover or lid on the reaction machine can be closed after this step to prevent the evaporation of acetone. In step 50, tocopherol (the main ingredient of Vitamin E) is added to the existing acetone, Ethanol, Methy Ethyl Ketone, DME, glycerin and water mixture, and then mixed for one minute at 25 degrees Celcius in the reaction machine. In step 60, the perfume is added to the existing Vitamin E, acetone, Ethanol, Methy Ethyl Ketone, DME, glycerin and water mixture, and then mixed for one minute at 25 degrees Celcius in the reaction machine. In step 60, the existing perfume, Vitamin E, acetone, Ethanol, Methy Ethyl Ketone, DME, glycerin and water mixture is then mixed for five hours at 30 degrees Celcius in the reaction machine to maintain the resulting product at its optimum condition. In step 70, a sample of about 0.1 liters of the resulting product (i.e., artificial nail remover) is taken and tested. The testing is to determine the effectiveness of the nail remover in removing an ABS nail. In step 80, if the resulting product passes the test, it (i.e., the artificial nail remover) is stored. In one non-limiting embodiment, the artificial nail remover is stored in an aluminum can, and applied by the user via the use of a spray.

In use, the user can take the spray can containing the artificial nail remover of the present invention, and then spray the remover at an ABS nail. Ideally, about 0.3 ml is sprayed and the ABS nail will begin to melt after about 30 seconds.

Thus, the artificial nail remover of the present invention is effective in removing an artificial nail, yet has added components that are directed to minimize chlorosis and the removal of fat, to moisturize and otherwise supplement the user's skin, and to counter or offset the normal strong and unpleasant odor of acetone.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method of removing an artificial nail, comprising:
    providing an artificial nail remover that comprises acetone, methyl ethyl ketone, ethanol, dimethyl esters, Glycerine, water, vitamin E, and a perfume; and
    applying the artificial nail remover to an ABS nail.

2. An artificial nail remover that comprises acetone, methyl ethyl ketone, ethanol, dimethyl esters, Glycerine, water, vitamin E, and a perfume.

3. The remover of claim 2, wherein the acetone is less than or equal to 40% by total volume.

4. The remover of claim 2, wherein the dimethyl esters is less than or equal to 15% by total volume.

5. The remover of claim 2, wherein the glycerine is less than or equal to 7% by total volume.

6. The remover of claim 2, wherein the vitamin E is less than or equal to 1% by total volume.

7. The remover of claim 2, wherein the perfume is less than or equal to 4% by total volume.

8. The remover of claim 2, wherein the perfume is a solution that gives off a fragance.

* * * * *